US00PP12511P2

(12) United States Plant Patent

Olesen et al.

(10) Patent No.: US PP12,511 P2

(45) Date of Patent: Apr. 2, 2002

(54) SHRUB ROSE PLANT NAMED 'POULOR'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/274,683

(22) Filed: Mar. 24, 1999

(51) Int. Cl.[7] ..... A01H 5/00

(52) U.S. Cl. ..... Plt./107

(58) Field of Search ..... Plt./107, 128, 102

(56) References Cited

PUBLICATIONS

Copy of DK PBR 15764, granted Feb. 3, 1994, and Grant #3681 granted Feb. 3, 1993.*

Copy of PL PBR ROA0222, filed Aug. 31, 1995 and Grant #000740, granted Feb. 2, 1998.*

Copy of NL PBR R002159, filed Aug 1, 1994 and Grant #14755, granted Jan. 31, 1995.*

Copy of QZ PBR 950596, filed Aug. 8, 1995 and Grant #EU0353, granted Aug. 2, 1996.*

OPOV–ROM, 2000/04, Plant Variety Database, GTI Jouve Retrieval software, 4 citations for 'POULor'.*

* cited by examiner

*Primary Examiner*—Howard J. Locker

(57) ABSTRACT

A new garden rose plant which has abundant, pink flowers and attractive, disease resistant foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between two unnamed seedlings.

The two parents were crossed and the resulting seeds were planted in a controlled environment. The new variety is named 'POULor'.

The new rose may be distinguished from its seed parent, an unnamed seedling, created by the same inventors, by the following combination of characteristics:

1. The seed parent has soft yellow blooms; whereas 'POULor' has pink blooms;

2. The seed parent is lower growing and more spreading than 'POULor'.

The new variety may be distinguished from its pollen parent, an unnamed seedling, created by the same inventors, by the following combination of characteristics:

1. The pollen parent is of the floribunda class while 'POULor' is a shrub rose;

2. The pollen parent's growth habit is more upright than 'POULor';

3. The pollen parent's blooms are a darker pink when compared to the blooms of 'POULor'.

The objective of the hybridization of this rose variety for garden use was to create a new and distinct variety with unique qualities, such as:

1. Uniform and abundant flowers;

2. Vigorous, compact growth;

3. Disease resistant foliage;

4. Continuous blooming over the growing season.

This combination of qualities is not present in previously available commercial cultivars of this type and distinguishes 'POULor' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULor' was selected in the Spring 1987 by the inventors as a single plant from the aforementioned hybridization.

Asexual reproduction of 'POULor' by traditional budding was first done by L. Pernille and Mogens N. Olesen in August 1987 in a nursery in Fredensborg, Denmark. This initial and other subsequent propagations conducted in controlled environments have demonstrated that the characteristics of 'POULor' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULor'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULor', as observed in its outdoor growth in a field nursery in Jackson County, Oreg. Observations were conducted during September, 1998. Color references are made using The Royal Horticultural Society (London, England) Colour Chart, 1995, except where common terms of color are used.

For a comparison, several physical characteristics of the rose variety 'POULans', a shrub rose variety, from the same inventors, described and illustrated in U.S. Plant Pat. No. 9,664 and issued on Oct. 22, 1996 are compared to 'POULor' in Chart 1.

CHART 1

| | 'POULor' | 'POULans' |
|---|---|---|
| Bloom size when fully open. | Small, 35–45 mm. | 45–55 cm |
| Plant size. | 70 cm (h) × 60 cm (w). | 90–120 cm (h) × 90–120 (w). |
| Petalage. | Semi-double, 14–18 petals. | Semi-Double, 18–26 petals. |

Parents:

*Seed parent.*—Unnamed seedling.

*Pollen parent.*—Unnamed seedling.

Classification:

*Botanical.*—*Rosa hybrida.*

*Commercial.*—Shrub.

FLOWER AND FLOWER BUD

Blooming habit: Continuous.

Flower bud:

*Size.*—Upon opening, 9 mm–11 mm in length from base of receptacle to end of bud.

*Bud form.*—Short, pointed ovoid.

*Bud color.*—As sepals unfold, Red-Purple Group 63B. Red-Purple Group 67D at ¼ opening.

*Sepals.*—Green Group 143C. Medium foliaceous appendages on three of the five sepals. Surfaces of sepals moderately pubescent. Stipitate glands are present along the margins and outer surface of sepals.

*Receptacle.*—Surface: Large number of stipitate hairs. Shape: Urn-shaped. Size: Medium to large. 5 mm (h)×6 mm (w). Color: Yellow-Green Group 144A.

*Peduncle.*—Surface: Smooth. Length: 40 mm to 50 mm average length. Length to first set of leaves is 20–25 mm. Color: Yellow-Green Group 144A. Strength: Semi-erect to pendulant.

*Pedicel.*—Color: Yellow-Green Group 144A, with intonations of Greyed-Red Group 180C. Length: 40 to 50 mm. Surface: Smooth.

*Borne.*—Multiple buds per stem, with 5–25 buds per flowering stem.

Flower bloom:

*Fragrance.*—Very light. However the stipitate glands on pedicel give a spicy clove scent.

*Duration.*—As a cut flower 2 to 4 days. The individual blooms have a duration on the plant of approximately 1 to 3 days. Petals fall cleanly away from plant.

*Size.*—Small, with the average flower diameter is 35–45 mm when open.

*Form.*—Semi-double. Shape of flower when viewed from the side: Upon opening, upper part: Flattened convex. Upon opening, lower part: Flattened convex. Open flower, upper part: Flat. Open flower, lower part: Concave.

*Petalage.*—Semi-double, Average range: 14–18 petals under normal conditions with few petaloids.

Color:

*Upon opening, petals.*—Outermost petals: Upper Surface: Red-Purple Group 64D with streaks of white and flecks and intonation of Red-Purple Group 67B. Reverse Side: Red-Purple Group 67B. Innermost petals: Upper Surface: Red-Purple Group 64C. Reverse Side: Red-Purple Group 67D with vertical thin white streaks (White Group 155B).

*Upon opening, basal petal spots.*—Outermost petals: Outer Side: Green-Yellow Group 1C. Inner Side: Green-Yellow Group 1A. Innermost petals: Outer Side: Green-Yellow Group 1B with basal portion of petal having a color of Green-Yellow 1C. Inner Side: Green-Yellow Group 1B at basal spot with basal portion of petal having a color of Green-Yellow Group 1C.

*After opening, petals.*—Outermost petals: Upper Surface: Red-Purple Group 68B. Reverse Side: Red-Purple Group 68B with some petals exhibiting thin vertical white stripes. Innermost petals: Upper Surface: Red-Purple Group 66C. Substantial variegations on petals. Variegation color is variable ranging from White Group 155D to Yellow Group 2D. Red-Purple Group 73B. Reverse Side: Red-Purple Group 73B.

*After opening, basal petal spots.*—Outermost petals: Outer Side: Green-Yellow Group 1B transition to Yellow-White 158D in basal portion of the petals. Inner Side: Green-Yellow Group 1B with transition in basal portion of petal of White Group 155D. Innermost petals: Outer Side: Yellow Group 2A. Inner Side: Yellow Group 2B.

General tonality: On open flower, Red-Purple Group 65A. No change in the general tonality at the end of the 3rd day. Afterwards, general tonality is Red Group 65C.

Petals:

*Petal reflex.*—Slightly.

*Petal edge.*—With Point in center of margin.

*Shape.*—Obovate.

*Petaloids.*—Present, with 0–3 petaloids observed.

*Thickness.*—Thin.

*Arrangement.*—Informal.

Reproductive organs:

*Pollen.*—Color: Greyed-Orange Group 163A. Quantity: Abundant.

*Anthers.*—Size: Small. Color: Greyed-Orange Group 163D. Quantity: Abundant.

*Filaments.*—Color: Green-Yellow Group 1A.

*Stigmas.*—Few female flower parts. Stigmas are inferior in position to the anthers. Anthers and filaments are curved inward and conceal stigmas when pollen is most abundant. Color: Yellow-Green Group 150D.

*Styles.*—Color: Yellow-Green Group 144C. Limited number of styles have vertical streaking of Red-Purple Group 58C.

*Hips.*—None observed.

PLANT

Plant growth: Vigorous, compact, somewhat spreading. When grown as a budded field grown plant on *Rosa*

*multiflora* understock, the average height of the plant itself is 70 cm and the average width is 60 cm.

Stems:

*Color*.—Young wood: Yellow-Green Group 143C. Older wood: Yellow-Green Group 143B.

*Thorns*.—Incidence: Moderate. Size: Average length: 3 mm–5 mm. Color: Yellow-Green Group 151A. Shape: Convex.

*Surface*.—Young wood: Smooth. Older wood: Smooth.

Plant foliage: Quantity of leaflets on leaves in middle of the stem: 7 leaflets, occasionally 5 leaflets.

*Leaf size*.—Medium, 100–120 mm (l)×70–85 mm (w).

*Quantity*.—Above average.

*Color*.—Upper Leaf Surface: Yellow-Green Group 146A. Lower Leaf Surface: Yellow-Green Group 146D. Juvenile foliage: Upper Surface: Green Group 137C. Lower Surface: Green Group 143B. Anthocyanin: None observed.

*Venation*.—Reticulate.

Plant leaves and leaflets:

*Stipules*.—Size: 14 mm–18 mm. Color: Green Group 143A. Stipitate glands: Along margins of stipule and on the bottom of the stipule.

*Petiole*.—Length: 20 mm. Color: Green Group 143A. Underneath: Small number of prickles and a moderate number of stipitate glands. Margins: Stipitate glands present at edges.

*Rachis*.—Color: Yellow-Green Group 144A. Underneath: Prickles every 15 mm. Stipitate glands present at intersection of leaf and rachis. Margins: Very limited number of stipitate glands along margin.

*Leaflet*.—Edge: Serrated. Shape: Ovate. Texture: Glossy, thin.

Disease resistance: Exceptional resistance to mildew, black spot, and Botrytis under normal growing conditions in Jackson County, Oreg.

Cold hardiness: 'POULor' has been found to be cold hardy in Fredensborg, Denmark and in Jackson County, Oreg.

We claim:

1. A new and distinct variety of rose plant of the shrub class, substantially as herein illustrated and described as a distinct and novel rose variety due to its abundant, pink flowers, vigorous growth, disease resistance, and extended period of bloom.

* * * * *

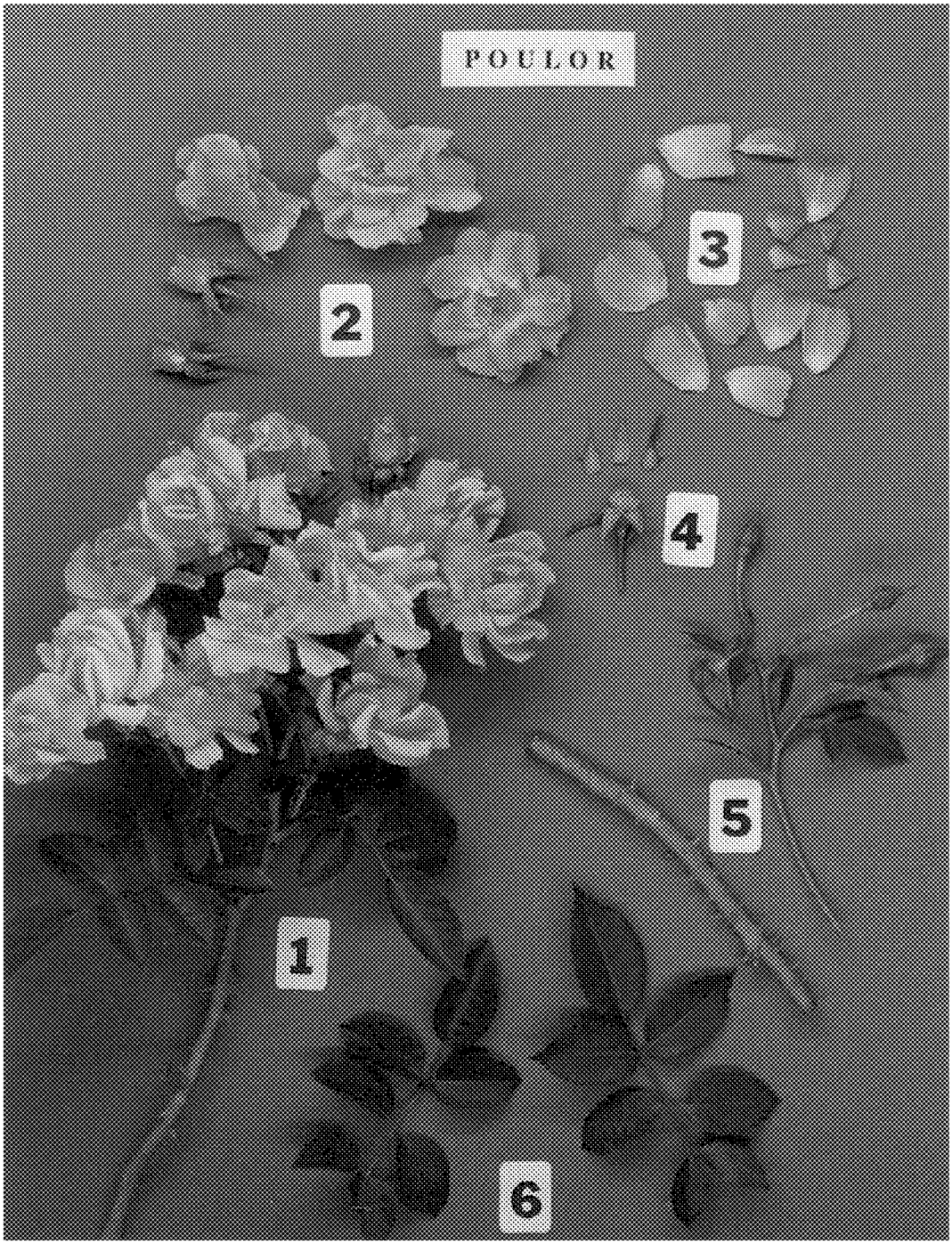
POULOR
1
2
3
4
5
6